(12) United States Patent
Takahashi (10) Patent No.: US 7,947,226 B2
(45) Date of Patent: May 24, 2011

(54) CATALYTIC COMBUSTION TYPE GAS SENSOR, SENSING ELEMENT AND COMPENSATING ELEMENT FOR THE SAME

(75) Inventor: Ikuo Takahashi, Tokorozawa (JP)

(73) Assignee: Citizen Holdings Co, Ltd., Tokyo (JP)

( * ) Notice: Subject to any disclaimer, the term of this patent is extended or adjusted under 35 U.S.C. 154(b) by 236 days.

(21) Appl. No.: 12/295,177

(22) PCT Filed: Mar. 29, 2007

(86) PCT No.: PCT/JP2007/056902
§ 371 (c)(1),
(2), (4) Date: Sep. 29, 2008

(87) PCT Pub. No.: WO2007/114267
PCT Pub. Date: Oct. 11, 2007

(65) Prior Publication Data
US 2009/0249859 A1  Oct. 8, 2009

(30) Foreign Application Priority Data
Mar. 31, 2006 (JP) .................. 2006-100258

(51) Int. Cl.
*G01N 33/00* (2006.01)
(52) U.S. Cl. .......................... 422/94; 422/83
(58) Field of Classification Search ............ 422/94, 422/83
See application file for complete search history.

(56) References Cited

U.S. PATENT DOCUMENTS
2005/0220672 A1  10/2005  Takahashi et al.

FOREIGN PATENT DOCUMENTS

| EP | 0206839 A2 | 12/2008 |
|---|---|---|
| GB | 2125554 A | 3/1984 |
| JP | 62-8048 A | 1/1987 |
| JP | 03-162658 A | 7/1991 |
| JP | 11-132980 A | 5/1999 |
| JP | 2000-292399 A | 10/2000 |
| JP | 2002-139469 A | 5/2002 |
| JP | 2004-69436 A | 3/2004 |
| JP | 3624928 B2 | 3/2005 |
| JP | 2005-315845 A | 11/2005 |

OTHER PUBLICATIONS

European Search Report dated Apr. 23, 2009, issued in corresponding European Patent Application No. 07740340.0. Williams, Geraint et al.; "The semistor: a new concept in selective methane detection", Sensors and Actuators B, vol. 57, 1999, pp. 108-114.
International Search Report of PCT/JP2007/056902, date of mailing, Jun. 26, 2007.

*Primary Examiner* — Sam P Siefke
(74) *Attorney, Agent, or Firm* — Westerman, Hattori, Daniels & Adrian, LLP (57) ABSTRACT

A sensing element for catalytic combustion type gas sensor includes: a heat conducting layer (12); a heater coil (13) buried in the heat conducting layer (12); and a combustion catalyst layer (11) coating or carried by a surface of the heat conducting layer (12) and causing combustion of a detection target gas brought into contact therewith, wherein the combustion catalyst layer (11) and the heat conducting layer (12) are both made of a firing material whose main component is tin oxide. Preferably, the heat conducting layer (12) is made of fine powder of the firing material, the firing material being produced by firing at a higher temperature than a temperature for producing the firing material of the combustion catalyst layer (11). Accordingly, durability and waterproof performance of the gas sensor itself can be enhanced, and without the need to take measures such as special environment setting, mounting thereof on a FCV can be realized.

14 Claims, 7 Drawing Sheets

SENSOR MAIN BODY

US 7,947,226 B2

CATALYTIC COMBUSTION TYPE GAS SENSOR, SENSING ELEMENT AND COMPENSATING ELEMENT FOR THE SAME

TECHNICAL FIELD

The present invention relates to a sensing element and a compensating element for a catalytic combustion type gas sensor detecting the leakage of various kinds of gases, and a catalytic combustion type gas sensor including these elements.

BACKGROUND TECHNOLOGY

Figure 13:
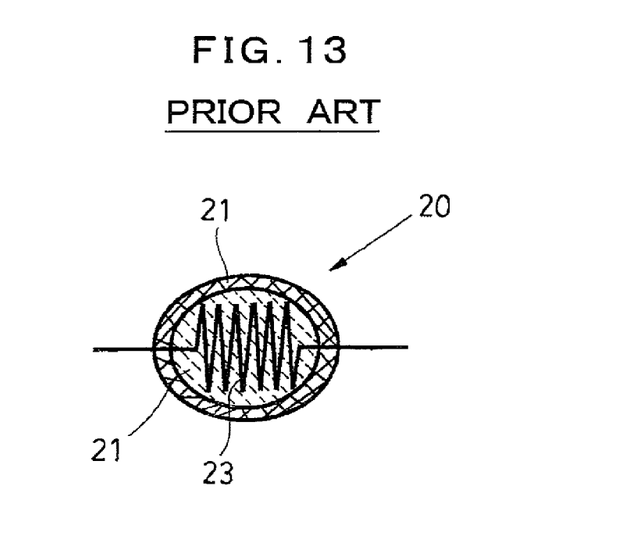
FIG. 13 is a cross-sectional view showing an example of a conventional sensing element for catalytic combustion type gas sensor, taken along a longitudinal direction.

As a sensor detecting flammable gas such as hydrogen gas and methane gas, a catalytic combustion type gas sensor has conventionally been known. As shown in FIG. 13, for instance, the catalytic combustion type gas sensor uses a sensing element 20 in which a heater coil 23 is buried in a heat conducting layer (catalyst carrier) 22 whose surface is coated with or carries a combustion catalyst layer 21 causing combustion of a detection target gas brought into contact therewith, and the heater coil 23 of the sensing element 20 is heated to a predetermined temperature in advance by supplying electricity therethrough, and when flammable gas comes into contact with the combustion catalyst layer 21 to burn, a change in resistance value of the heater coil 23 occurs due to a temperature increase caused by the combustion and is detected as voltage, whereby the presence of the flammable gas is detected (for example, see a patent document 1).

Figure 14:
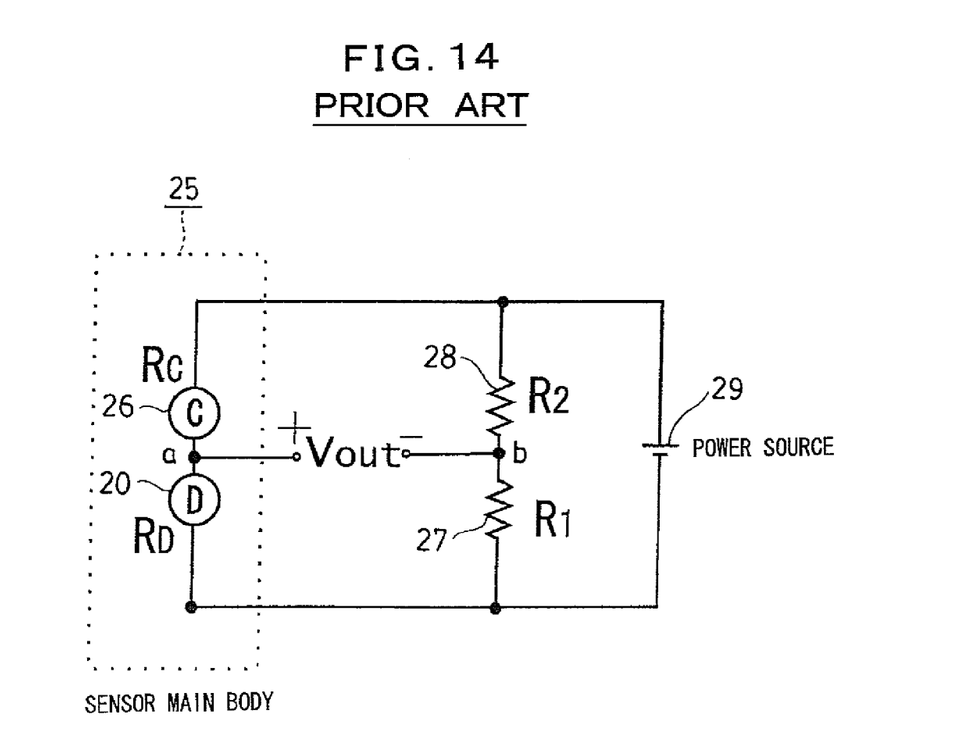
FIG. 14 is a diagram showing a basic circuit configuration of a conventional catalytic combustion type gas sensor.

Further, the same patent document 1 describes a gas sensor as shown in FIG. 14 in whose sensor main body 25, a compensating element 26 (resistance value $R_C$) is serially connected to the sensing element 20 (resistance value $R_D$) in order to cancel the influence by a change in ambient temperature, and this series circuit is connected in parallel to a series circuit composed of two serial-connected fixed resistance elements 27 (resistance value R1) and 28 (resistance value R2), thereby forming a Wheatstone bridge circuit. Direct-current voltage is applied by a power source 29 between both ends of the parallel circuit, and output voltage Vout between a connection point a of the sensing element 20 and the compensating element 26 and a connection point b of the two resistance elements 27, 28 is detected. As the compensating element 26 in this case, used is a element in which a heater coil having the same electric characteristic as that of the sensing element 20 is buried in a heat conducting layer coated with a compensating material layer instead of the combustion catalyst layer.

The aforesaid output voltage Vout of the Wheatstone bridge circuit is dependent on a balance of the electrify resistances ($R_D$ and $R_C$) of the sensing element 20 and the compensating element 26. In a clean atmosphere, the resistance value $R_D$ and the resistance value $R_C$ are determined in a balanced state between heat generation amounts of the heater coils in the sensing element 20 and the compensating element 26 and amounts of heat dissipated into the atmosphere, and the output voltage Vout shows a zero-point value. When the detection target gas comes into contact with the sensing element 20, the temperature of the sensing element 20 increases due to catalytic combustion, and thus only the resistance value $R_D$ increases, resulting in an increase in the output voltage Vout, and the target gas is detected based on an amount of this increase.

By the way, in recent years, the practical application of a fuel cell vehicle (hereinafter, abbreviated as "FCV") which does not use fossil fuel such as gasoline and thus does not involve a possibility of causing air pollution due to exhaust gas has been started, and it is stipulated as compulsory that the FCV is equipped with a gas sensor for high-sensitivity detection of hydrogen leakage.

However, automobile components go through severe tests, for example, dew condensation is made to occur in the components and dew is frozen, or the components are repeatedly ON-OFF operated while exposed to 90° vapor. In all of these tests, moisture is given to the automobile components to check their durability, and components mounted on the FCV are also required to have the same durability.

The catalytic combustion type gas sensor is considered as one of sensors having an operation principle with high total adaptability as a hydrogen sensor for FCV, but cannot be said to have high waterproof performance because of its structure.

The reason for this will be briefly described. A sensing element and a compensating element in a conventional catalytic combustion type gas sensor has a cross-sectional structure as shown in FIG. 13, and the sensing element 20 has a sponge-like cross-sectional structure allowing the permeation of hydrogen so that hydrogen combustion activity can be obtained also in a thickness direction of the combustion catalyst layer 21, and thus steam, minute water droplets, and the like can enter the combustion catalyst layer 21.

Further, materials forming the combustion catalyst layer 21 are "tin oxide+iron oxide+platinum fine powder+palladium fine powder+others", and the combustion catalyst layer 21 exhibits a high characteristic with respect to a retaining capability of water droplets and the like owing to a hydrophilic property of these materials.

The compensating material layer of the compensating element does not have a sponge-like cross sectional structure, but it has a hydrophilic property as in the sensing element because its constituent materials are "tin oxide+copper oxide+others".

On the other hand, the heat conducting layers positioned on inner sides of the combustion catalyst layer and the compensating material layer of the sensing element and the compensating element have a dense structure and their constituent materials are "alumina+titania (titanium oxide)+boron nitride+bismuth oxide glass+others" and so on, and the heat conducting layers exhibit a hydrophobic property owing to these factors.

Therefore, these constituent layers peel off each other in a high-humidity environment due to a difference in hydrous property therebetween. In particular, when dew condensation occurs in the sensing element and the compensating element and the dew is frozen, the combustion catalyst layer and the compensating material layer drop from surfaces of the heat conducting layers. Consequently, the electrify resistance values of the sensing element and the compensating element change from initial values and accordingly, a zero point output value of the output voltage of the Wheatstone bridge circuit greatly fluctuates, resulting in error detection.

Therefore, some FCV makers take measures which involve high cost factors, such as setting a special environment for protecting a hydrogen sensor from water, and improvement in waterproof performance of the hydrogen sensor itself is required in order to promote wider use of the FCV.

As a technique for enhancing durability of such a conventional gas sensor, it has been proposed in, for example, a patent document 2, that a heater heating a detection target gas is provided adjacent to and on an upstream side of a gas sensor installation position in a channel through which the detection target gas flows, thereby preventing dew condensation in the gas sensor.

Patent document 1: JP H 3-162658A
Patent document 2: JP 2004-69436A

DISCLOSURE OF THE INVENTION

Problems to be Solved by the Invention

However, preventing the occurrence of the dew condensation in the gas sensor by the heater heating the detection target gas is only a symptomatic treatment means even if this measure is adopted in the catalytic combustion type gas sensor and cannot enhance durability and waterproof performance of the catalytic combustion type gas sensor itself.

The invention was made in view of such a background, and its object is to enhance durability and waterproof performance of a catalytic combustion type gas sensor itself and to thereby make it possible to mount the catalytic combustion type gas sensor on a FCV without taking measures such as special environment setting. To attain the object, there is provided a sensing element and a compensating element for catalytic combustion type gas sensor which have high durability and waterproof performance, and there is further provided a catalytic combustion type gas sensor including the sensing element and the compensating element.

Means for Solving the Problems

A sensing element for catalytic combustion type gas sensor according to the invention is a sensing element which includes a heat conducting layer, a heater coil buried in the heat conducting layer, and a combustion catalyst layer coating or carried by a surface of the heat conducting layer and causing combustion of a detection target gas brought into contact therewith, and in order to attain the above objects, the combustion catalyst layer and the heat conducting layer are both made of a firing material whose main component is tin oxide.

Preferably, the heat conducting layer is made of fine powder of the firing material whose main component is tin oxide, the firing material being produced by the firing at a higher temperature than a temperature for producing the firing material of the combustion catalyst layer.

More preferably, at least one of platinum and palladium is added to the firing material of the heat conducting layer.

Desirably, the fine powder of the firing material forming the heat conducting layer is bound by bismuth oxide-based low-melting point glass.

A compensating element for catalytic combustion type gas sensor according to the invention is a compensating element which includes a heat conducting layer, a heater coil buried in the heat conducting layer, and a compensating material layer coating or carried by a surface of the heat conducting layer, and in order to attain the above objects, the compensating material layer and the heat conducting layer are both made of a firing material whose main component is tin oxide.

Preferably, the heat conducting layer is made of fine powder of the firing material whose main component is tin oxide, the firing material being produced by the firing at a higher temperature than a temperature for producing the firing material of the compensating material layer.

Desirably, the fine powder of the firing material forming the heat conducting layer is bound by bismuth oxide-based low-melting point glass.

To attain the above objects, a catalytic combustion type gas sensor according to the invention includes the above-described sensing element and compensating element for catalytic combustion type gas sensor according to the invention, and a first series circuit in which the heater coil of the sensing element and the heater coil of the compensating element are serially connected and a second series circuit in which a first resistance element and a second resistance element are serially connected are connected in parallel to form a Wheatstone bridge circuit.

Further, a direct-current voltage is applied between connection points of the first series circuit and the second series circuit, and a voltage between a connection point of the sensing element and the compensating element and a connection point of the first resistance element and the second resistance element is output as a detection signal of a detection target gas.

The detection target gas can be any of various flammable gases, but the invention is especially effective for detecting hydrogen gas.

Effect of the Invention

According to the catalytic combustion type gas sensor of the invention, it is possible to enhance durability and waterproof performance of the sensing element and the compensating element, and accordingly durability and waterproof performance of the sensor itself can be enhanced, which makes it possible to mount the catalytic combustion type gas sensor on a FCV without taking measures such as special environment setting.

REFERENCE OF NUMERALS

1: sensor main body of catalytic combustion type gas sensor
3: mount base
4, 5: electrode pin
7: first resistance element
8: second resistance element
9: power source
10: sensing element
11: combustion catalyst layer
12, 12': heat conducting layer of sensing element
13: heater coil of sensing element
30: compensating element
31: compensating material layer
32: heat conducting layer of compensating element
33: heater coil of compensating element

BEST MODE FOR CARRYING OUT THE INVENTION

Hereinafter, the best mode for carrying out the invention will be concretely described based on the drawings.

First, an embodiment of a sensing element and a compensating element for catalytic combustion type gas sensor according to the invention will be described by using FIG. 1 to FIG. 6.

Figure 1:
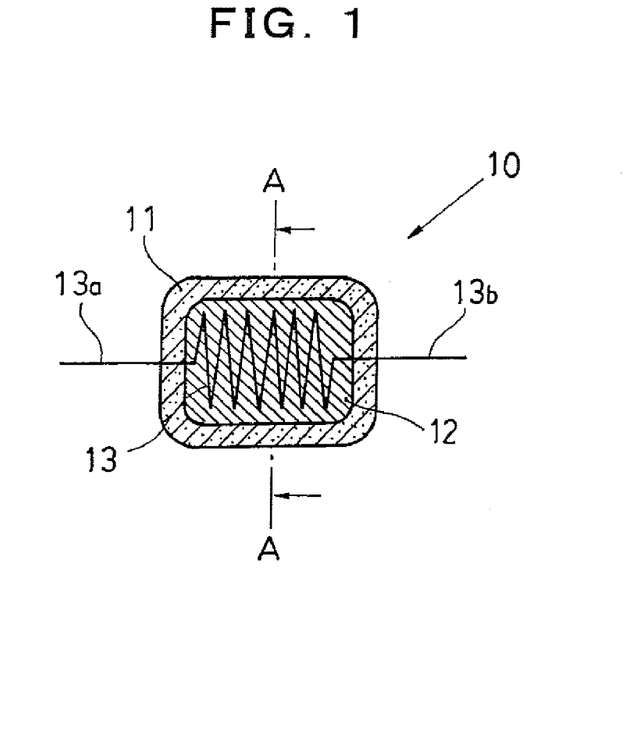
FIG. 1 is a cross-sectional view showing an embodiment of a sensing element for catalytic combustion type gas sensor according to the invention, taken along a longitudinal direction.
Figure 3:
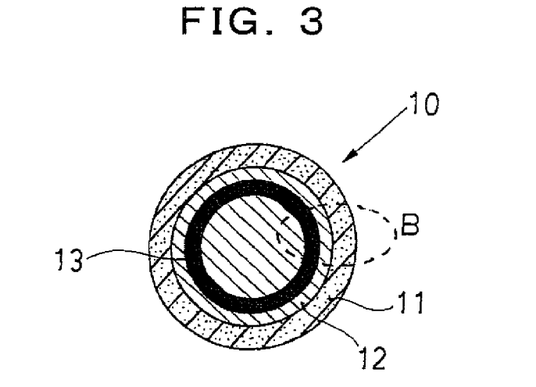
FIG. 3 is an enlarged cross-sectional view of the sensing element taken along the A-A line in FIG. 1.

FIG. 1 is a cross-sectional view of the sensing element taken along its longitudinal direction and FIG. 3 is a cross-sectional view taken along the A-A line in FIG. 1. In the sensing element 10, a bead section of a heater coil 13 is buried in a heat conducting layer 12, and a surface of the heat conducting layer 12 is coated with a combustion catalyst layer (also called an oxidation catalyst layer) 11 which is a catalyst layer causing oxidation combustion of a detection target gas brought into contact therewith.

The heater coil 13 is made of a platinum wire or a wire of a platinum-based alloy such as a platinum-rhodium alloy. Preferably, a portion to be the bead section is formed as a double-wound coil in such a manner that, for example, an original wire with a wire diameter of about 10 μm to about 50 μm, more preferably, about 20 μm to about 30 μm is wound around a core bar to form a single-wound coil, and this coil is wound around a core bar again. This structure increases a contact area between the heater coil 13 and the heat conducting layer 12 and further increases a resistance value, realizing high gas sensitivity. Further, since lead sections 13a, 13b are also single-wound coils and thus can absorb external impact, realizing a highly impact-resistant sensor. However, this structure is not restrictive, and a generally used conventional heater coil, that is, a heater coil whose bead section is a single-wound coil and whose lead sections are linear may be used.

The heat conducting layer 12 and the combustion catalyst layer 11 can have an improved waterproof property in a high-humidity environment when they have a small difference in hydrous property and have physical affinity. However, in realizing this, no change is made in the combustion catalyst layer 11 in view of a gas sensitivity property, and a material of the heat conducting layer 12 is changed to the material of the combustion catalyst layer 11.

Therefore, the heat conducting layer 12 and the combustion catalyst layer 11 of the sensing element 10 are both made of a firing material whose main component is tin oxide.

More preferably, the combustion catalyst layer 11, similarly to that of the conventional sensing element, is made of a firing material which contains as its main component tin oxide ($SnO_2$) and additionally contains iron oxide when necessary, with platinum (Pt) and palladium (Pd) in fine powder form dispersed as a catalyst and which is produced by firing a mixture of these components in the atmosphere at a temperature of about 600° C., and this combustion catalyst layer 11 coats the surface of the heat conducting layer 12.

As the heat conducting layer 12, tin oxide is used instead of conventionally used alumina and titania. However, preferably, tin oxide for the heat conducting layer is firing in the atmosphere at a high temperature of 1100° C. to 1200° C. unlike tin oxide for the combustion catalyst layer, and has a lower content of water of crystallization than tin oxide for the combustion catalyst layer which is firing at 600° C., and fine powder of the firing material is used to form the heat conducting layer 12.

Further, preferably, at least one of platinum and palladium, preferably both are added to tin oxide for the heat conducting layer. This eliminates a need for an intermediate layer of platinum-palladium which is set on an interface between the heat conducting layer and the combustion catalyst layer of the conventional sensing element and moreover, can improve gas detection sensitivity. Conventionally, in order to set the intermediate layer, in a manufacturing process of the sensing element, a platinum-palladium solution is applied on a surface of the alumina-titania-based heat conducting layer and this solution is heat-treated, whereby the intermediate layer is formed on the surface of the heat conducting layer. According to this embodiment, a process of forming the intermediate layer can be eliminated.

Further, in this embodiment, bismuth oxide-based low-melting point glass is mixed in the fine powder of the aforesaid tin oxide-based firing material for the heat conducting layer to bind the fine powder. Consequently, minute pores are distributed inside, which allows the detection target gas to enter the heat conducting layer 12.

Figure 6:
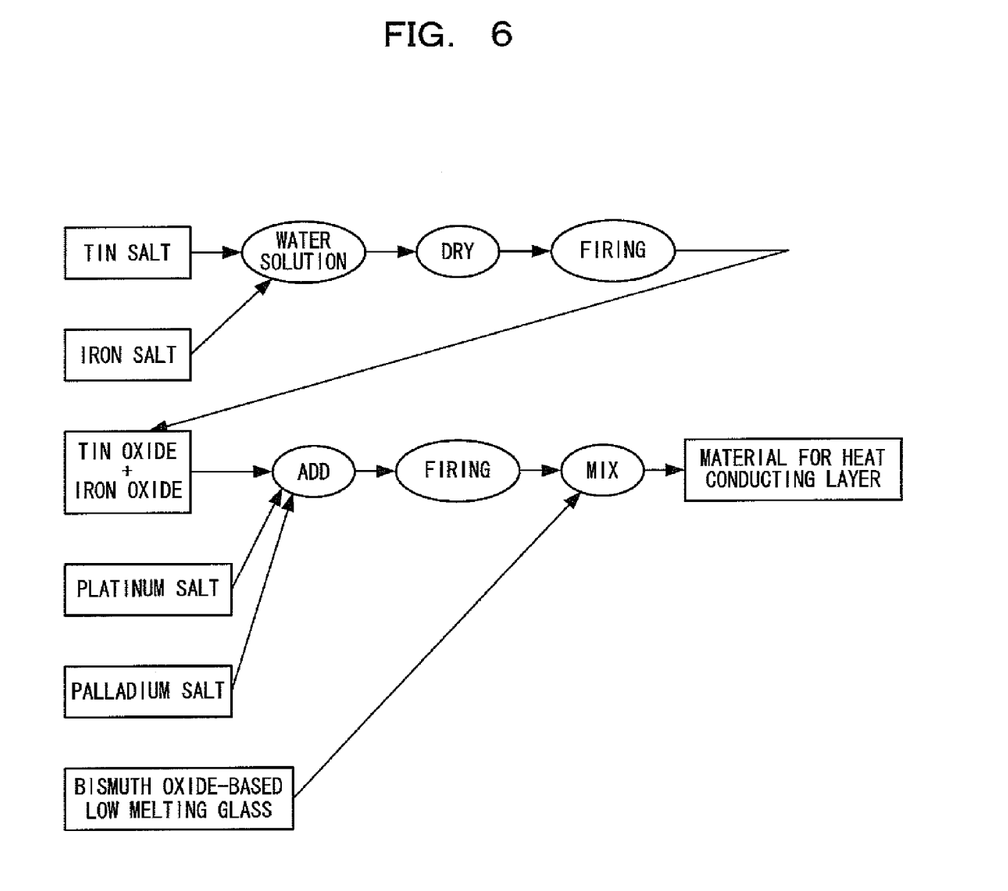
FIG. 6 is a flowchart to illustrate processes for manufacturing a material of a heat conducting layer used in the invention.

Processes for manufacturing such a preferable material for the heat conducting layer used in the sensing element of the invention will be described with reference to the flowchart shown in FIG. 6.

First, tin salt and iron salt are dissolved in water, and the resultant water solution is dried and burnt. Platinum salt and palladium salt are added to a thus produced firing material made of tin oxide and iron oxide, and the resultant is firing again, and its fine powder and bismuth oxide-based low-melting point glass are mixed, thereby producing the material for the heat conducting layer.

The reason why the fine powder is used as the material of the heat conducting layer is to avoid the formation of a void layer in the heat conducting layer, thereby preventing deterioration of the heat conducting performance.

As a result of changing the heat conducting layer in the above-described manner, the conventionally occurring drop of the combustion catalyst layer from the surface of the heat conducting layer is eliminated even when dew condensation occurs in the sensing element 10 and dew is frozen, and as a result, durability and waterproof performance of the sensing element for catalytic combustion type gas sensor are greatly enhanced.

Figure 4:
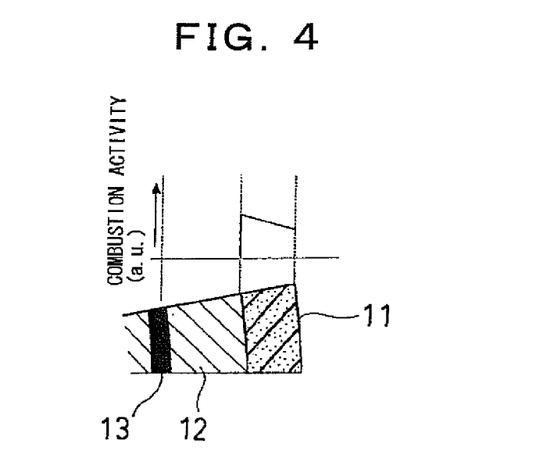
FIG. 4 is an enlarged view of a portion surrounded by the broken line B in FIG. 3 and showing combustion activity.
Figure 5:
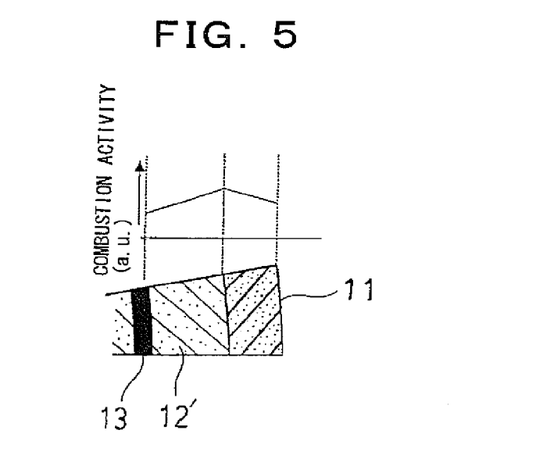
FIG. 5 is a view similar to FIG. 4, of another example of the invention.

In a case where neither platinum nor palladium is added to the material of the heat conducting layer 12, combustion activity, though high in the combustion catalyst layer 11, is low in the heat conducting layer 12 as shown in FIG. 4, so that catalytic combustion of flammable gas does not occur in the heat conducting layer 12. On the other hand, adding at least one of platinum and palladium to the material of the heat conducting layer 12 results in higher combustion activity also in the heat conducting layer 12 as shown in FIG. 5. Consequently, the catalytic combustion of flammable gas occurs in the whole area of the combustion catalyst layer 11 up to the inside of the heat conducting layer 12, resulting in improved sensitivity for detecting flammable gas.

Figure 2:
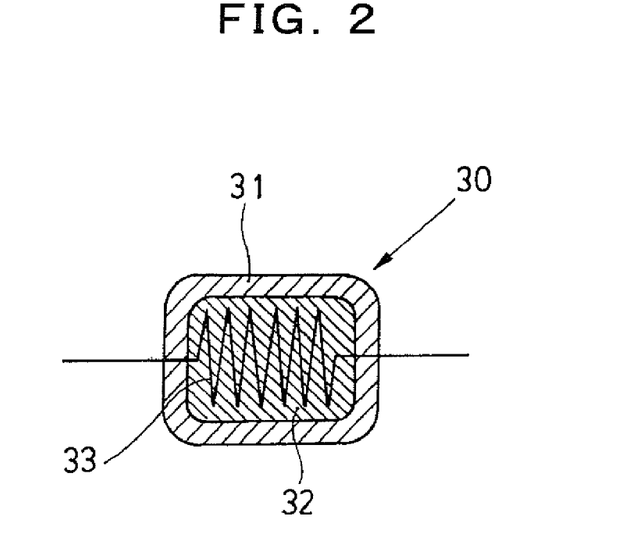
FIG. 2 is a cross-sectional view showing an embodiment of a compensating element for catalytic combustion type gas sensor according to the invention, taken along a longitudinal direction.

FIG. 2 is a cross-sectional view showing an embodiment of the compensating element for catalytic combustion type gas sensor according to the invention, taken along the longitudinal direction.

In the compensating element 30, a bead section of a heater coil 33 is buried in a heat conducting layer 32 and a compensating material layer 31 coats a surface of the heat conducting layer 32.

The heater coil 33 and the heat conducting layer 32 of the compensating element 30 are made of the same materials as those of the heater coil 13 and the heat conducting layer 12 of the sensing element 10 and are equal in heat capacity to the heater coil 13 and the heat conducting layer 12. Therefore, the heater coil 33 is made of a platinum wire or a wire of a platinum-based alloy such as a platinum-rhodium alloy.

The heat conducting layer 32 is made of a firing material whose main component is tin oxide instead of conventionally used alumina and titania.

Similarly to the combustion catalyst layer 11 of the sensing element 10, the compensating material layer 31 is made of a firing material whose main component is tin oxide, with copper oxide or the like being added thereto, and is formed to be equal in heat capacity to the combustion catalyst layer 11. However, neither platinum nor palladium as an oxidation catalyst is added.

Preferably, as the firing material of the heat conducting layer 32, whose main component is tin oxide, used is fine powder of a firing material whose main component is tin oxide and which is produced by firing at a higher temperature than a temperature for producing the firing material of the compensating material layer 31. Further, preferably, the fine powder of the firing material forming the heat conducting layer is bound by bismuth oxide-based low-melting point glass. These points are the same as in the aforesaid heat conducting layer 12 of the sensing element 10, and therefore detailed description thereof will be omitted.

In this compensating element 30, it is also possible to realize physical affinity of the heat conducting layer and the compensating material layer by changing the material of the heat conducting layer, and therefore, even when dew condensation occurs and dew is frozen in the compensating element 30, the conventionally occurring drop of the compensating material layer from the surface of the heat conducting layer does not occur, resulting in great enhancement of durability and water proof performance of the compensating element for catalytic combustion type gas sensor.

Figure 7:
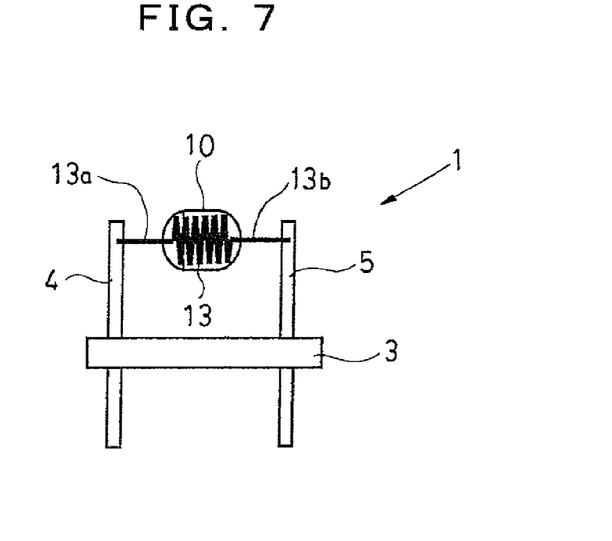
FIG. 7 is a front view of a sensor main body, showing how the sensing element is attached in a catalytic combustion type gas sensor according to the invention.

Next, an embodiment of the catalytic combustion type gas sensor according to the invention will be described with reference to FIG. 7 and FIG. 8. FIG. 7 is a front view of a sensor main body.

The sensor main body 1 shown in FIG. 7 has a plate-shaped mount base 3 made of ceramic or resin, and the above-described sensing element 10 for catalytic combustion type gas sensor according to the invention is fixed in such a manner that lead sections 13a, 13b, which project from both ends, of its heater coil 13 are attached to electrode pins 4, 5 for external connection penetrating through the mount base 3.

Further, the above-described compensating element 30 for catalytic combustion type gas sensor according to the invention, though not shown, is fixedly set in line with the sensing element 10, similarly by having both lead sections of the heater coil 33 attached to another pair of electrode pins.

The sensing element 10 and the compensating element 30 are surrounded by the mount base 3 and a not-shown gas permeable explosion-proof structure made of a wire gauze or a sintered body of metal powder or ceramic powder.

Figure 8:
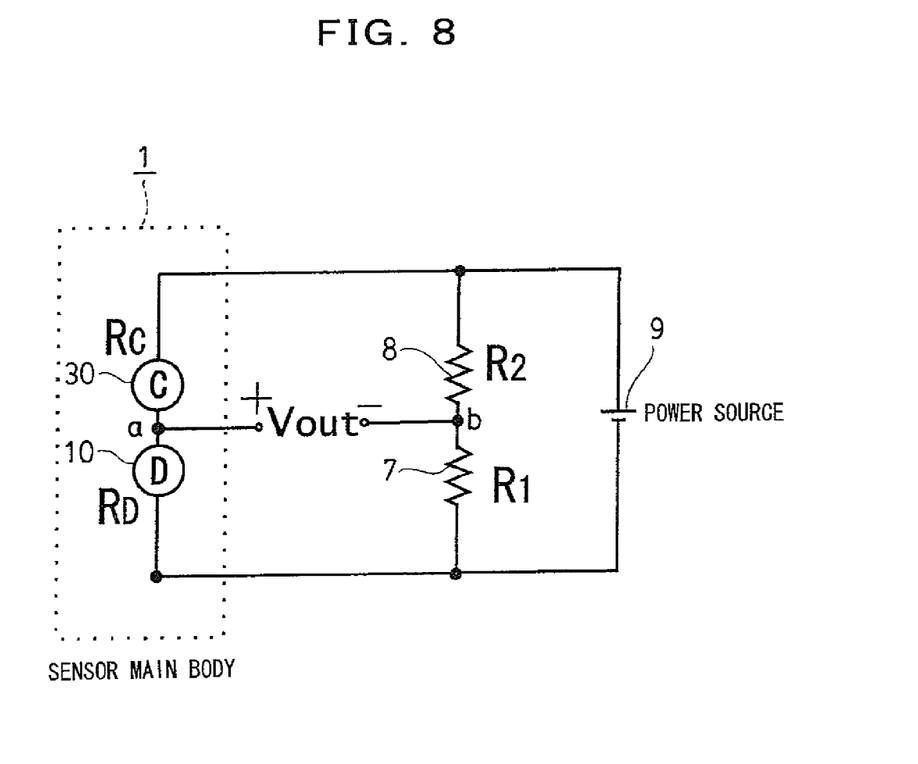
FIG. 8 is a diagram showing a basic circuit configuration of the catalytic combustion type gas sensor according to the invention.

FIG. 8 shows a basic circuit configuration of the catalytic combustion type gas sensor according to the invention, and is a diagram of a circuit including a Wheatstone bridge circuit and a power source applying a direct-current voltage to the Wheatstone bridge circuit.

A first serial circuit in which the above-described sensing element (D element) 10 and compensating element (C element) 30 of the sensor main body 1 are serially connected and a second series circuit in which a first resistance element 7 and a second resistance element 8 are serially connected are connected in parallel to form the Wheatstone bridge circuit. A power source 9 applies the direct-current voltage between connection points of the first series circuit and the second series circuit, and a voltage Vout between a connection point a of the sensing element 10 and the compensating element 30 and a connection point b of the first resistance element 7 and the second resistance element 8 is output as a detection signal of the detection target gas.

Here, the output voltage Vout of the Wheatstone bridge circuit is zero volt (0 mV) when $R_1 \times R_2 = R_D \times R_C$, where $R_D$, $R_C$, $R_1$, and $R_2$ are electrify resistance values of the sensing element 10, the compensating element 30, the first resistance element 7, and the second resistance element 8 respectively. Desirably, as the first resistance element 7 and the second resistance element 8, those having the same resistance value and the same temperature characteristic are used.

When the power source 9 which can vary output voltage applies a rated voltage to the series circuit composed of the heater coil of the sensing element 10 and the heater coil of the compensating element 30, an operating temperature is generated in the sensing element 10 and the compensating element 30, so that the output voltage Vout is obtained, the output voltage Vout being dependent on the electrify resistance values $R_D$, $R_C$ in a balanced state between heat supply components from the heater coils in the respective elements and a heat release component dissipated to the atmosphere in a clean atmosphere. The output voltage at this time is also called "a zero point value". If the detection target gas is present and it comes into contact with the combustion catalyst layer 11 of the sensing element 10 shown in FIG. 1 to burn, the temperature of the heater coil 13 increases and only its energizing resistance value $R_D$ increases, and therefore, an increase in the output voltage Vout to a plus (+) side by an amount corresponding to gas sensitivity occurs and can be detected.

Examples of the detection target gas are methane gas, hydrogen gas, LP gas (liquefied petroleum gas), propane gas, butane gas, ethylene gas, and carbon monoxide gas, or organic component gas such as ethanol and acetone.

The catalytic combustion type gas sensor, when mounted on a fuel cell vehicle (FCV), can detect leakage of hydrogen gas with high sensitivity.

The catalytic combustion type gas sensor has remarkably improved durability and waterproof performance owing to the use of the sensing element 10 and the compensating element 30 according to the invention, and thus can pass a severe test for automobile components.

Figure 9:
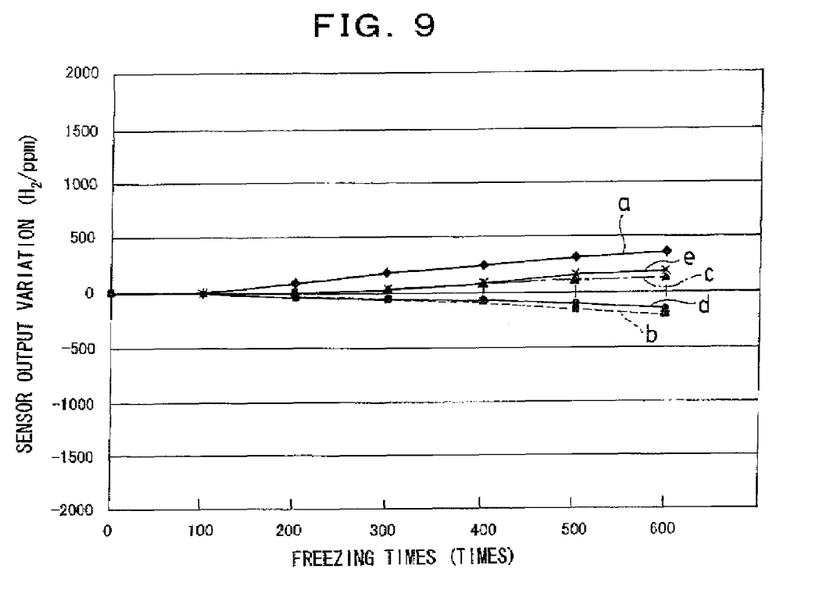
FIG. 9 is a graph showing the result of a freezing test conducted on catalytic combustion type gas sensors each using a sensing element and a compensating element whose heat conducting layers have the specifications according to the invention.
Figure 10:
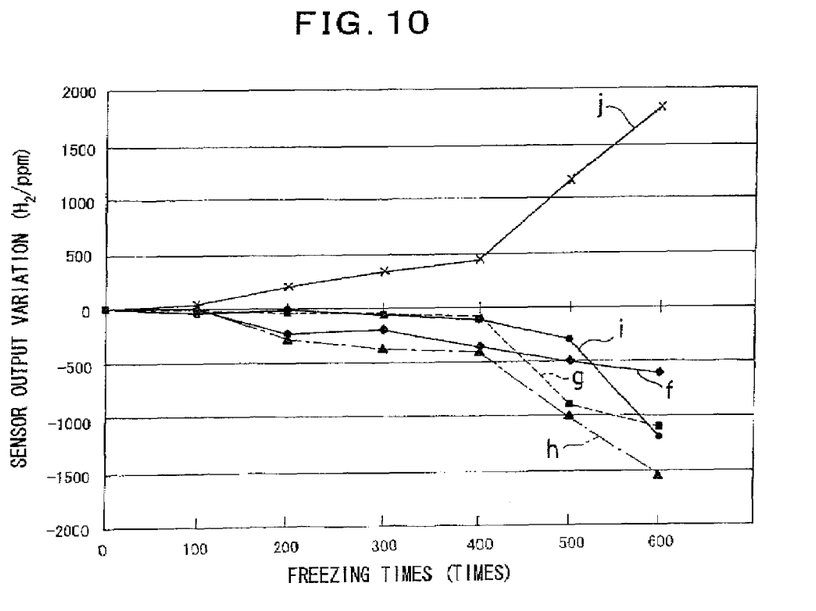
FIG. 10 is a graph showing the result of a freezing test conducted on catalytic combustion type gas sensors each using a sensing element and a compensating element whose heat conducting layers have conventional specifications.
Figure 11:
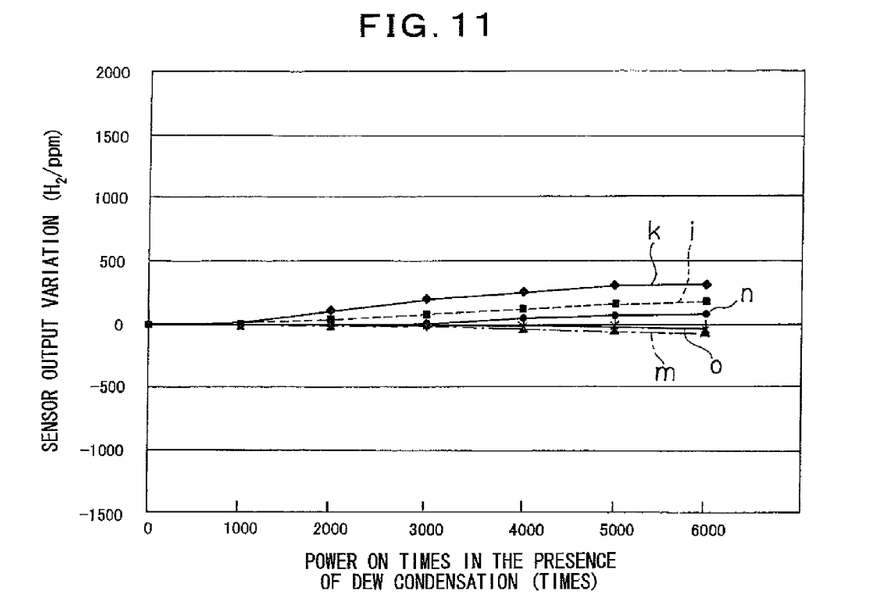
FIG. 11 is a graph showing the result of a power ON-OFF test in the presence of dew condensation, conducted on catalytic combustion type gas sensors each using a sensing element and a compensating element whose heat conducting layers have the specifications according to the invention.
Figure 12:
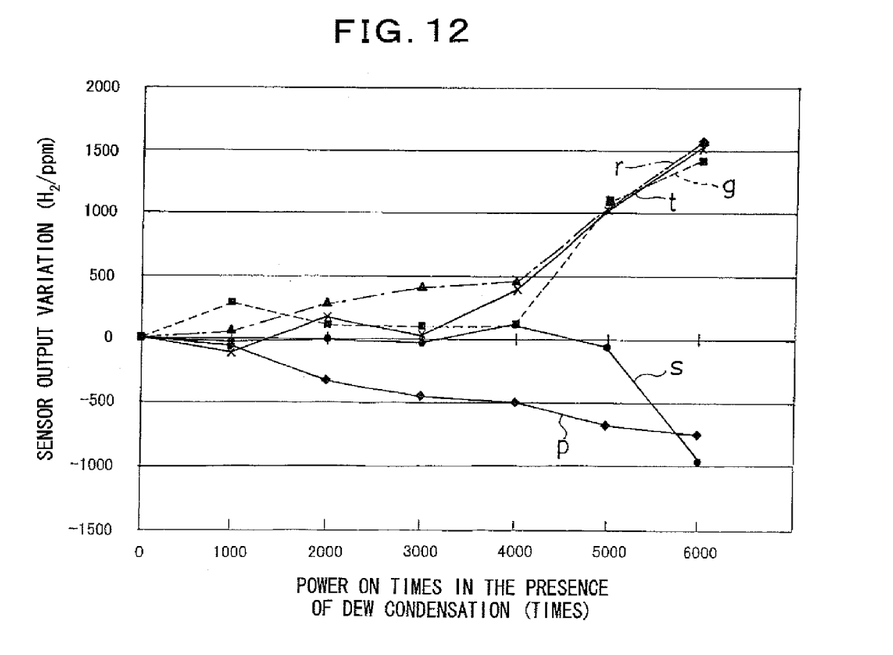
FIG. 12 is a graph showing the result of a power ON-OFF test in the presence of dew condensation, conducted on catalytic combustion type gas sensors each using a sensing element and a compensating element whose heat conducting layers have the conventional specifications.

Table 1, Table 2, FIG. 9, and FIG. 10 show the results of freezing tests, and Table 3, Table 4, FIG. 11, and FIG. 12 show the results of power ON-OFF tests in the presence of dew condensation. As the detection target gas, hydrogen ($H_2$) gas is used and a unit of sensor output variation is [$H_2$/ppm].

Table 1 and FIG. 9 are data showing the result of the freezing test conducted on catalytic combustion type gas sensors each using a sensing element and a compensating element whose heat conducting layers have the specifications according to the invention, and even when the number of freezing times reaches 600 times, the sensor output variation is within ±500 [$H_2$/ppm] even for a sample with the maximum sensor output variation.

In contrast, Table 2 and FIG. 10 are data showing the result of the freezing test conducted on catalytic combustion type gas sensors each using a sensing element and a compensating element whose heat conducting layers have the conventional specifications, and when the number of freezing times exceeds 400 times, it is seen that the sensor output variation rapidly increases to exceed ±500 [$H_2$/ppm] and the breakage of one of or both of the sensing element and the compensating element starts to occur.

Table 3 and FIG. 11 show data of the power ON-OFF test in the presence of dew condensation, conducted on catalytic combustion type gas sensors each using a sensing element and a compensating element whose heat conducting layers have the specifications according to the invention, and it is seen that, when the number of power ON times in the presence of dew condensation reaches 6000 times, the sensor output variation is within ±500 [$H_2$/ppm] even for a sample with the maximum sensor output variation.

Table 4 and FIG. 12 show data of the power ON-OFF test in the presence of dew condensation, conducted on catalytic combustion type gas sensors each using a sensing element and a compensating element whose heat conducting layers have the conventional specifications, and it is seen that, when the number of power ON times in the presence of dew condensation exceeds 4000 times, the sensor output variation rapidly increases to exceed ±500 [$H_2$/ppm], and the breakage of one of or both of the sensing element and the compensating element starts to occur.

It should be noted that the structures, shapes, materials, manufacturing methods, and so on of the catalytic combustion type gas sensor according to the invention and its sensing element and compensating element are not limited to those in the above-described embodiment, and it goes without saying that appropriate changes can be made in matters except the matters described in the claims.

TABLE 1

| number of freezing | heat conducting layer with the specifications according to the invention | | | | |
|---|---|---|---|---|---|
| times | a | b | c | d | e |
| 0 | 0 | 0 | 0 | 0 | 0 |
| 100 | 0 | −3 | 7 | −12 | 9 |
| 200 | 83 | −32 | 10 | −31 | 13 |
| 300 | 172 | −78 | 42 | −88 | 40 |
| 400 | 249 | −113 | 91 | −105 | 85 |
| 500 | 312 | −198 | 109 | −134 | 121 |
| 600 | 367 | −220 | 153 | −181 | 186 |

TABLE 2

| number of freezing | heat conducting layer with the conventional specifications (unit: $H_2$/ppm) | | | | |
|---|---|---|---|---|---|
| times | f | g | h | i | j |
| 0 | 0 | 0 | 0 | 0 | 0 |
| 100 | −32 | −62 | −12 | −82 | 51 |
| 200 | −292 | −126 | −281 | −6 | 193 |
| 300 | −203 | −85 | −386 | −94 | 328 |
| 400 | −408 | −145 | −426 | −117 | 434 |
| 500 | −528 | −916 | −1052 | −282 | 1144 |
| 600 | −600 | −1126 | −1545 | −1192 | 1810 |

TABLE 3

| number of ON times | heat conducting layer with the specifications according to the invention | | | | |
|---|---|---|---|---|---|
| | k | l | m | n | o |
| 0 | 0 | 0 | 0 | 0 | 0 |
| 1000 | 16 | 23 | −3 | 5 | −2 |
| 2000 | 91 | 41 | −18 | 17 | −17 |
| 3000 | 189 | 69 | −32 | 22 | −21 |
| 4000 | 223 | 98 | −49 | 38 | −34 |
| 5000 | 289 | 130 | −66 | 44 | −49 |
| 6000 | 307 | 164 | −87 | 67 | −62 |

TABLE 4

| number of ON times | heat conducting layer with the conventional specifications (unit: $H_2$/ppm) | | | | |
|---|---|---|---|---|---|
| | p | q | r | s | t |
| 0 | 0 | 0 | 0 | 0 | 0 |
| 1000 | −84 | 308 | 70 | −58 | −145 |
| 2000 | −343 | 171 | 283 | −2 | 192 |
| 3000 | −481 | 154 | 413 | −79 | 55 |
| 4000 | −508 | 153 | 467 | 176 | 406 |
| 5000 | −700 | 1121 | 1097 | −112 | 1010 |
| 6000 | −769 | 1420 | 1548 | −982 | 1534 |

INDUSTRIAL APPLICABILITY

The sensing element, the compensating element, and the catalytic combustion type gas sensor according to the invention are widely applicable as a gas leakage detector in apparatuses and systems using various kinds of flammable gases or in rooms where they are installed, and so on. In particular, a fuel cell whose rapid practical application in future is desired uses flammable hydrogen gas as its fuel, and thus needs be equipped with a sensor detecting hydrogen leakage, and it is compulsory to install a hydrogen gas sensor in each section inside a fuel cell vehicle. Further, it is indispensable to provide a hydrogen gas sensor also in a fuel cell system and the like used as an auxiliary power source for industrial use or for home use, and the application of the invention is extremely effective in these hydrogen gas sensors.

What is claimed is:

1. A sensing element for catalytic combustion type gas sensor, comprising:
a heat conducting layer;
a heater coil buried in said heat conducting layer; and
a combustion catalyst layer coating or carried by a surface of said heat conducting layer and causing combustion of a detection target gas brought into contact therewith, wherein
said combustion catalyst layer is made of a firing material whose main component is tin oxide, and
said heat conducting layer is made of a firing material whose main component is tin oxide, the firing material being produced by the firing at a temperature of 1100° C. to 1200° C. which is higher than a temperature of around 600° C. which the firing material of said combustion catalyst layer has been produced.

2. The sensing element for catalytic combustion type gas sensor according to claim 1,
wherein said heat conducting layer is made of fine powder of the firing material whose main component is tin oxide, the firing material being produced by the firing at a higher temperature than a temperature for producing the firing material of said combustion catalyst layer.

3. The sensing element for catalytic combustion type gas sensor according to claim 1,
wherein at least one of platinum and palladium is added to the firing material of said heat conducting layer.

4. The sensing element for catalytic combustion type gas sensor according to claim 2,
wherein the fine powder of the firing material forming said heat conducting layer is bound by bismuth oxide-based low-melting point glass.

5. The sensing element for catalytic combustion type gas sensor according to claim 4,
wherein at least one of platinum and palladium is added to the firing material of said heat conducting layer.

6. A compensating element for catalytic combustion type gas sensor comprising:
a heat conducting layer;
a heater coil buried in said heat conducting layer; and
a compensating material layer coating or carried by a surface of said heat conducting layer,
wherein
said compensating material layer is made of a firing material whose main component is tin oxide, and
said heat conducting layer is made of a firing material whose main component is tin oxide, the firing material being produced by the firing at a temperature of 1100° C. to 1200° C. which is higher than a temperature of around 600° C. which the firing material of said compensating material layer has been produced.

7. The compensating element for catalytic combustion type gas sensor according to claim 6,
wherein said heat conducting layer is made of fine powder of the firing material whose main component is tin oxide, the firing material being produced by the firing at a higher temperature than a temperature for producing the firing material of said compensating material layer.

8. The compensating element for catalytic combustion type gas sensor according to claim 7,
wherein the fine powder of the firing material forming said heat conducting layer is bound by bismuth oxide-based low-melting point glass.

9. A catalytic combustion type gas sensor comprising:
a sensing element for catalytic combustion type gas sensor and a compensating element for catalytic combustion type gas sensor,
wherein said sensing element comprises: a heat conducting layer; a heater coil buried in the heat conducting layer; and a combustion catalyst layer coating or carried by a surface of the heat conducting layer and causing combustion of a detection target gas brought into contact therewith, and the combustion catalyst layer is made of a firing material whose main component is tin oxide, and the heat conducting layer of the sensing element is made of a firing material whose main component is tin oxide, the firing material being produced by the firing at a temperature of 1100° C. to 1200° C. which is higher than a temperature of around 600° C. which the firing material of said combustion catalyst layer has been produced,
wherein the compensating element comprises: a heat conducting layer; a heater coil buried in the heat conducting layer; and a compensating material layer coating or carried by a surface of the heat conducting layer, and the compensating material layer is made of a firing material whose main component is tin oxide, and the heat conducting layer of the compensating element is made of a firing material whose main component is tin oxide, the firing material being produced by the firing at a temperature of 1100° C. to 1200° C. which is higher than a temperature of around 600° C. which the firing material of said compensating material layer has been produced,
wherein a first series circuit in which the heater coil of said sensing element and the heater coil of said compensating element are serially connected and a second series circuit in which a first resistance element and a second resistance element are serially connected are connected in parallel to form a Wheatstone bridge circuit, and
wherein a direct-current voltage is applied between connection points of the first series circuit and the second series circuit, and a voltage between a connection point of said sensing element and said compensating element and a connection point of the first resistance element and the second resistance element is output as a detection signal of a detection target gas.

10. The catalytic combustion type gas sensor according to claim 9,
wherein the heat conducting layer of said sensing element is made of fine powder of the firing material whose main component is tin oxide, the firing material being produced by the firing at a higher temperature than a temperature for producing the firing material of the combustion catalyst layer, and
wherein the heat conducting layer of said compensating element is made of fine powder of the firing material whose main component is tin oxide, the firing material being produced by the firing at a higher temperature than a temperature for producing the firing material of the compensating material layer.

11. The catalytic combustion type gas sensor according to claim 10,
wherein the fine powder of the firing materials forming each of the heat conducting layer of said sensing element and the heat conducting layer of said compensating element is bound by bismuth oxide-based low-melting point glass.

12. The catalytic combustion type gas sensor according to claim 9,
wherein at least one of platinum and palladium is added to the firing material of the heat conducting layer of said sensing element.

13. The catalytic combustion type gas sensor according to claim 9, wherein the detection target gas is hydrogen gas.

14. The catalytic combustion type gas sensor according to claim 12, wherein the detection target gas is hydrogen gas.

* * * * *